US00PP33084P2

(12) United States Plant Patent
Solano Ramirez

(10) Patent No.: US PP33,084 P2
(45) Date of Patent: May 18, 2021

(54) ***SALVIA* PLANT NAMED 'BALMIRROBI'**

(50) Latin Name: *Salvia greggii*
Varietal Denomination: Balmirrobi

(71) Applicant: Ball Horticultural Company, West Chicago, IL (US)

(72) Inventor: Rolando Solano Ramirez, Guadalupe, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/005,593

(22) Filed: Aug. 28, 2020

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./475
See application file for complete search history.

*Primary Examiner* — Susan McCormick Ewoldt
(74) *Attorney, Agent, or Firm* — Audrey Charles

(57) ABSTRACT

A new and distinct cultivar of *Salvia* plant named 'Balmirrobi', characterized by its medium rose and light cream bicolored flowers, medium green-colored foliage, and moderately vigorous, upright-mounded growth habit, is disclosed.

1 Drawing Sheet

Latin name of genus and species of plant claimed: *Salvia greggii*.

Variety denomination: 'Balmirrobi'.

BACKGROUND OF THE INVENTION

The present invention relates to a new and distinct cultivar of *Salvia* plant botanically known as *Salvia greggii* and hereinafter referred to by the cultivar name 'Balmirrobi'.

The new cultivar originated in a controlled breeding program in Guadalupe, Calif. during June 2016. The objective of the breeding program was the development of *Salvia* cultivars that bloom throughout the summer and have upright-mounded growth habits.

The new *Salvia* cultivar was the result of a self-pollination of the proprietary *Salvia greggii* breeding selection coded Sal30922-4-2-4, not patented, characterized by its white-colored flowers, medium green-colored foliage, and moderately vigorous, mounded growth habit. The new cultivar was selected as a single flowering plant within the progeny of the above stated self-pollination during June 2017 in a controlled environment in Guadalupe, Calif.

Asexual reproduction of the new cultivar by terminal stem cuttings since June 2017 in Guadalupe, Calif. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balmirrobi' as a new and distinct cultivar of *Salvia* plant:

1. Medium rose and light cream bicolored flowers;
2. Medium green-colored foliage; and
3. Moderately vigorous, upright-mounded growth habit.

Plants of the new cultivar differ from plants of the parent primarily in having medium rose and light cream bicolored flowers.

Of the many commercially available *Salvia* cultivars, the most similar in comparison to the new cultivar is Mirage Neon Rose 'Balmirsal', U.S. Plant Pat. No. 30,729. However, in comparison, plants of the new cultivar differ from plants of 'Balmirsal' in at least the following characteristics:

1. Plants of the new cultivar have a bicolor medium rose and light cream lower lip while plants of 'Balmirsal' have salmon-colored flowers; and
2. Plants of the new cultivar have lighter colored bracts than plants of 'Balmirsal'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balmirrobi'. The plants were approximately four months old. The plants were grown in one-gallon containers for approximately 9 weeks in an outdoor nursery in West Chicago, Ill. Plants were given two pinches prior to transplant.

DETAILED BOTANICAL DESCRIPTION

Figure 1:
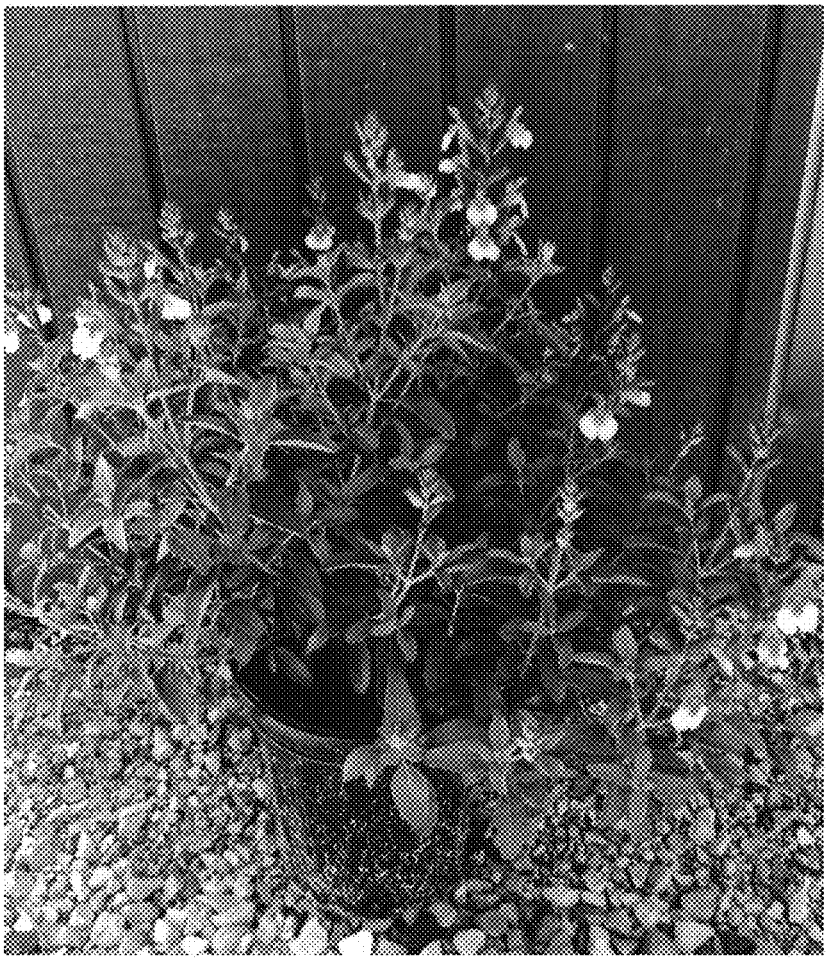
FIG. 1 illustrates a side view of the overall growth and flowering habit of 'Balmirrobi'.
Figure 2:
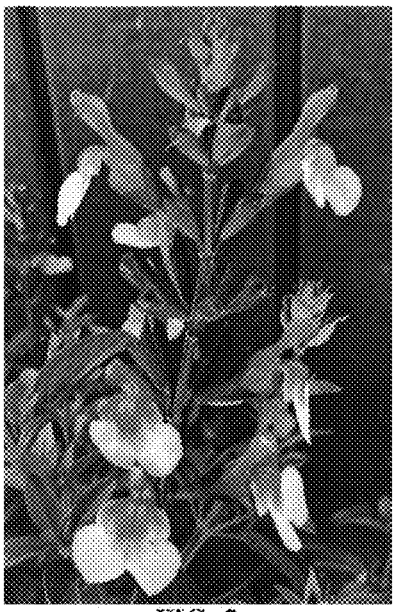
FIG. 2 illustrates a close-up view of an inflorescence of 'Balmirrobi'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2020 under natural light conditions in Naperville, Ill.

The following descriptions and measurements describe approximately four-month old plants produced from cuttings from stock plants and grown under conditions comparable to those used in commercial practice. The plants were grown in one-gallon containers for approximately 9 weeks in an outdoor nursery in West Chicago, Ill. Plants were given two pinches prior to transplant. Prior to transplant plants were grown in liners in a poly-covered greenhouse in West Chicago, Ill. Greenhouse temperatures ranged from an average high of 69.3° F. (20.7° C.) to an average low of 63.6° F. (17.6° C.), and supplemental lighting was provided daily for five hours during short days. Measurements and numerical values represent averages of typical plants.

Botanical classification: *Salvia greggii* 'Balmirrobi'.

Parentage:

*Female and male parents*.—Proprietary *Salvia greggii* breeding selection coded Sal30922-4-2-4, not patented.

Propagation:

*Type cutting*.—Terminal stem.

*Time to initiate roots*.—Approximately 10 to 12 days.

*Time to produce a rooted cutting*.—Approximately 35 to 42 days.

*Root description*.—Fine, fibrous white to light brown in color.

*Rooting habit*.—Freely branching.

Plant description:

*Commercial crop time*.—Approximately 8 to 10 weeks from a rooted cutting to finish in a 15 cm pot.

*Growth habit and general appearance*.—Subshrub, moderately vigorous, upright-mounded growth habit.

*Hardiness*.—USDA Zone 7a (0° F. to 5° F./−17.8° C. to −15° C.).

*Size*.—Height from soil level to top of plant plane: Approximately 32.0 cm. Width: Approximately 48.0 cm.

*Branching habit*.—Freely branching, pinching enhances lateral branching. Quantity of branches per plant: Approximately 4 main branches and approximately 38 lateral branches.

*Branch*.—Shape: Square in cross section. Strength: Moderately strong, young growth flexible. Length to base of inflorescence: Approximately 13.0 cm to 16.0 cm. Diameter: Approximately 3.0 mm to 4.0 mm. Length of central internode: Approximately 2.5 cm. Texture: Densely pubescent. Color of young stems: 146C. Color of mature stems: 146C, becoming woody 199B and 200C with age.

Foliage description:

*General description*.—Quantity of leaves per branch: Approximately 8. Fragrance: Strong, sage-like. Form: Simple. Arrangement: Opposite.

*Leaves*.—Aspect: Acute to perpendicular angle to stem. Shape: Elliptic. Margin: Crenulate. Apex: Rounded. Base: Obtuse. Venation pattern: Pinnate. Length of mature leaf: Approximately 3.3 cm. Width of mature leaf: Approximately 1.5 cm. Texture of upper surface and lower surfaces: Glabrous. Color of upper surface of young foliage: 137A with venation of 137C. Color of lower surface of young foliage: Closest to 138A with venation of 146D. Color of upper surface of mature foliage: 137B with venation of 137C. Color of lower surface of mature foliage: Closest to between 138A and 138B with venation of 146D.

*Petiole*.—Length: Approximately 9.0 mm. Diameter: Approximately 1.0 mm. Texture: Sparsely pubescent. Color: 146D.

Flowering description:

*Flowering habit*.—'Balmirrobi' is freely flowering under outdoor growing conditions blooming from early spring through late summer.

*Lastingness of individual floret*.—Approximately 4 to 5 days.

Inflorescence description:

*General description*.—Type: Raceme with typically two florets per node. Quantity of open inflorescences per plant: Approximately 36. Fragrance: Faint, sweet. Length or height of inflorescence: Approximately 7.0 cm to 13.0 cm. Width of inflorescence: Approximately 5.0 cm. Quantity of fully-open flowers per inflorescence: Approximately 2 to 4.

*Peduncle*.—Shape: Square in cross section. Strength: Strong. Aspect: Primarily erect. Length: Approximately 2.5 cm. Diameter: Approximately 2.0 mm. Texture: Densely pubescent. Color: 146B.

Flower description:

*Type*.—Single, zygomorphic.

*Bud*.—Rate of opening: Generally takes 2 to 3 days for bud to progress from first color to fully open flower.

*Bud just before opening*.—Shape: Obovoid. Length: Approximately 1.4 cm. Diameter: Approximately 5.0 mm. Texture: Densely pubescent. Color: Calyx of 146D with an overlay of N186A; petals of 63A through 63C tinted with 64A, pubescence of 64B.

*Corolla*.—Shape: Bilabiate, lower lip having three lobes, based fused. Width: Approximately 1.6 cm. Length: Approximately 1.9 cm. Depth: Approximately 2.8 cm.

*Upper lip*.—Shape: Hooded. Margin: Entire. Apex: Rounded. Length from throat: Approximately 1.1 cm. Width: Approximately 4.0 mm. Texture of inner surface: Glabrous. Texture of outer surface: Densely pubescent. Color of inner surface when first and fully open: NN155D. Color of outer surface when first and fully open: 63B with 64B.

*Lower lip*.—Shape of central lobe: Obovate, cupped. Shape of lateral lobes: Oblong. Margin of central lobe: Shallowly scalloped. Margin of lateral lobes: Entire. Apex of central lobe: Emarginate. Apex of lateral lobes: Rounded. Length from throat of central lobe: Approximately 1.5 cm. Width of central lobe: Approximately 1.6 cm. Length from throat of lateral lobes: Approximately 8.0 mm. Width of lateral lobes: Approximately 3.0 mm. Texture of upper and lower surfaces: Glabrous. Color of upper surface when first and fully open: 155D with center of 63A to 63B. Color of lower surface when first and fully open: 155D with an underlay of closest to 64C.

*Corolla tube*.—Length: Approximately 1.7 cm. Width: Approximately 7.0 mm. Texture of inner and outer surfaces: Glabrous. Color of inner surface: NN155D, translucent. Color of outer surface: 64A to 64B.

*Calyx*.—Shape: Tubular. Length: Approximately 1.1 cm. Diameter: Approximately 6.0 mm.

*Sepals*.—Quantity per flower: 3, fused. Shape: Obovate. Margin: Entire. Apex: Acuminate. Length: Approximately 1.1 cm. Width: Two of approximately 3.0 mm and one of approximately 6.0 mm. Texture of inner and outer surfaces: Densely pubescent. Color of inner surface: 147C with an overlay of N186A. Color of outer surface: 146D with an overlay of N186A.

*Bracts*.—Quantity: One bract located at the base of each developing floret, bracts abscise as florets mature. Length: Approximately 8.0 mm. Width: Approximately 4.0 mm. Texture of inner surface: Glabrous. Texture of outer surface: Densely pubescent. Color of inner surface: Closest to 155C with 146D at apex. Color of outer surface: 155C with venation and apex of 146D, tint of 64B that becomes darker with age.

*Pedicel*.—Strength: Strong, flexible. Aspect: At an acute angle. Length: Approximately 4.0 mm. Diameter: Approximately 1.0 mm. Texture: Densely pubescent. Color: 146D with a heavy overlay of N186A.

*Reproductive organs*.—Androecium: Stamen quantity: 2 per flower, dorsifixed, strongly curved. Stamen length: Approximately 1.2 cm. Filament length: Approximately 1.1 cm. Filament color: NN155D, opaque with tinting and pubescence of 70A in center. Anther shape: Narrowly elliptic to oblong. Anther length: Approximately 2.0 mm. Anther color: 13B. Pollen amount: Abundant. Pollen color: 13A. Gynoecium: Pistil quantity: 1 per flower, strongly curved. Pistil length: Approximately 2.8 cm. Stigma shape: Cleft, two-parted, curved. Stigma length: 3.0 mm. Stigma color: NN155D tinted with 70A. Style length: Approximately 2.2 cm. Style color: NN155D, opaque. Style texture: Glabrous with a vertical line of feather-like pubescence extending from the stigma for approximately 5.0 mm. Ovary length: Approximately 3.0 mm. Ovary color: 154D.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'Balmirrobi', substantially as herein illustrated and described.

* * * * *